United States Patent
Kalla et al.

(10) Patent No.: US 9,469,545 B2
(45) Date of Patent: Oct. 18, 2016

(54) HOLLOW SILICA PARTICLES, COMPOSITIONS COMPRISING THEM AND METHODS FOR MAKING SAME

(71) Applicant: The Procter & Gamble Company, Cincinnati, OH (US)

(72) Inventors: Karen Kay Kalla, Cincinnati, OH (US); Matthew David Butts, Rexford, NY (US); Darryl Stephen Williams, Richmond, VA (US); Sarah Elizabeth Genovese, Delmar, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/736,331

(22) Filed: Jun. 11, 2015

(65) Prior Publication Data
US 2015/0274539 A1  Oct. 1, 2015

Related U.S. Application Data

(62) Division of application No. 11/200,591, filed on Aug. 10, 2005, now Pat. No. 9,278,866.

(51) Int. Cl.
| | |
|---|---|
| *C01B 33/12* | (2006.01) |
| *A61K 8/11* | (2006.01) |
| *A61K 8/58* | (2006.01) |
| *A61K 8/81* | (2006.01) |
| *A61K 8/891* | (2006.01) |
| *A61K 8/894* | (2006.01) |
| *A61Q 1/02* | (2006.01) |
| *A61Q 1/06* | (2006.01) |
| *A61Q 19/00* | (2006.01) |
| *B01J 13/02* | (2006.01) |
| *C01B 33/18* | (2006.01) |
| *A61K 8/25* | (2006.01) |

(52) U.S. Cl.
CPC ............ *C01B 33/126* (2013.01); *A61K 8/11* (2013.01); *A61K 8/25* (2013.01); *A61K 8/585* (2013.01); *A61K 8/8117* (2013.01); *A61K 8/891* (2013.01); *A61K 8/894* (2013.01); *A61Q 1/02* (2013.01); *A61Q 1/06* (2013.01); *A61Q 19/00* (2013.01); *A61Q 19/007* (2013.01); *B01J 13/02* (2013.01); *C01B 33/12* (2013.01); *C01B 33/18* (2013.01); *A61K 2800/41* (2013.01); *A61K 2800/412* (2013.01); *C01P 2004/34* (2013.01); *C01P 2004/51* (2013.01); *C01P 2004/62* (2013.01)

(58) Field of Classification Search
None
See application file for complete search history.

(56) References Cited

U.S. PATENT DOCUMENTS

| 9,278,866 B2 * | 3/2016 | Kalla .................. A61K 8/11 |
| 2003/0086896 A1 | 5/2003 | Midha et al. |
| 2007/0036705 A1 | 2/2007 | Butts et al. |

FOREIGN PATENT DOCUMENTS

JP  2006142491 A  8/2006

* cited by examiner

*Primary Examiner* — Maury Audet
(74) *Attorney, Agent, or Firm* — Betty J. Zea

(57) ABSTRACT

Methods for making comprising hollow silica particles from a composition comprising a silicon-containing compound selected from the group consisting of tetraalkoxysilanes, trialkyloxysilanes and derivatives thereof, dialkoxysilanes and derivatives thereof, alkoxysilanes and derivatives thereof, silicone oligomers, oligomeric silsesquioxanes and silicone polymers distributed over a polymer template core that is eliminated from the particle in a two-stage heating process. The particles of the present invention have a substantially uniform particle size and exhibit low permeability to liquids.

11 Claims, 2 Drawing Sheets

HOLLOW SILICA PARTICLES, COMPOSITIONS COMPRISING THEM AND METHODS FOR MAKING SAME

CROSS REFERENCE TO RELATED APPLICATIONS

This application is a Divisional of U.S. application Ser. No. 11/200,591, filed Aug. 10, 2005.

FIELD OF INVENTION

The present invention relates generally to the field of silica particle synthesis. More specifically, the present invention relates to the field of synthesizing substantially uniform silica-based particles for use in personal care products which encapsulate a hollow interior.

BACKGROUND OF THE INVENTION

In the personal care industry, particularly with respect to personal care products for skin, there is a need for ingredients that provide coverage for age spots, blemishes, discolorations, etc., as well as provide a natural look. It is a well known problem that cosmetic products that provide good coverage have a mask-like, unnatural appearance. This is particularly true with titanium dioxide-based materials, the most common type of opacifiers found in cosmetics. Many cosmetic compositions have been reported that provide high coverage with some degree of "naturalness", however none have provided the level of naturalness that is highly desired by consumers without sacrificing the required coverage.

Examples of hollow particles have been previously described. However, previously described materials have significant shortcomings as potential opacifiers in cosmetic formulations. Co- and terpolymer systems made from vinylidene chloride and acrylonitrile, or from vinylidene chloride, acrylonitrile and methylmethacrylate have been reported (e.g. Expancel™). Unfortunately these types of materials are only readily available in particle sizes that exceed the sizes believed necessary to achieve maximum optical performance benefits in cosmetic uses. Styrene/acrylate hollow particles (e.g. Ropaque™, Rohm & Haas) are also known, however these particles do not provide the desired optical benefits in cosmetic formulations.

Hollow particles with polymer shells can be made by creating core/shell particles containing a core with hydrolyzable acid groups and a sheath, or shell, that is permeable to a base. Hollow particles with silica shells synthesized using a layer-by-layer electrostatic deposition technique on a template are also known. In addition, hollow particles have also been synthesized by depositing nanoparticles derived from alkoxysilanes on a template particle, as well as by condensation of sodium silicate on a template particle followed by template removal. However, such particles often show a lack of continuity in the particle surface and thus often exhibit unacceptable shell permeability. Further, none of the known and reported particles have been made according to a method that allows for creation of the particles in a desired, substantially uniform, narrow range with narrow particle size distributions and having acceptable permeability, or they otherwise involve numerous synthetic steps which make their production impractical for use in personal care applications.

SUMMARY OF THE INVENTION

It has been found that, in cosmetic formulations, hollow particles produced within a certain, predetermined particle size range, with a narrow particle size distribution, and exhibiting low permeability are capable of concurrently providing high coverage as well as a more natural appearance relative to known cosmetic formulations.

The present invention relates to a hollow silica particle made from a composition comprising a silicon-containing compound incorporating silicon atoms derived from one or more silicon compounds including tetraalkoxysilanes, trialkoxysilanes, dialkoxysilanes, alkoxysilanes, silicone oligomers, oligomeric silsesquioxanes, silicone polymers, and derivatives and mixtures thereof. These silicon compounds optionally can be functionalized with any organic group or mixture of groups, provided that such groups do not interfere with the production of the particles. The particles of the present invention have a substantially uniform particle size. The present invention also relates to use of the hollow silica particle in cosmetic compositions.

The present invention further relates to a method for making a hollow silica-containing particle. A template particle, such as, but not limited to, a polymer template particle, is created and characterized by having a narrow particle size distribution. A silane coupling agent is provided to the template mixture. A silicon-containing compound or mixture of compounds is then added and allowed to react under conditions that cause the deposition of a silica-containing shell onto the template particle to create a substantially uniform coating on the template particle. The template particle core is then eliminated from the resulting particle via heating, dissolution, or extraction, and preferably via a two step heating process, leaving a hollow silica particle having a shell with a substantially constant thickness, desired, low level of permeability to liquids, white in color, and an overall, narrow particle size distribution range.

As used herein, "cosmetic composition" means any color cosmetic, nail, or skin care product. "Cosmetic compositions" include, but are not limited to, products that leave color on the face, including foundation, blacks and browns (i.e., mascara), concealers, eye liners, brow colors, eye shadows, blushers, lip sticks, lip balms, face powders, solid emulsion compact, and so forth. The term "foundation" refers to liquid, cream, mousse, pancake, compact, concealer or like product created or reintroduced by cosmetic companies to even out the overall coloring of the skin. "Skin care products" include, but are not limited to, skin creams, moisturizers, lotions, and body washes.

As used herein, "hollow particles" are those that remain hollow when placed in or when contacted with liquids. There remains a continuous hollow void of substantial size when placed in or contacted with liquids. Further, they exhibit low permeablility. The interior hollow portion of the particle does not substantially fill or take up fluids such as fragrances, oils, materials for controlled release, water, or other fluids which may be present in the formulation.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein.

All measurements made are at 25° C., unless otherwise designated.

DETAILED DESCRIPTION OF THE INVENTION

1. Method of Making

The process for making the hollow particles of the present invention includes preparing a template particle, depositing a silica-containing shell onto the particle, and then removing the template material, leaving the hollow silica-containing shell of a predetermined, substantially similar dimension and having an acceptably low permeability to liquids. Acceptable permeability is that which allows for the preparation of cosmetic or other compositions that maintain their optical properties for a sufficient time period. Preferably, the template particle, having a certain, predetermined, particle size, with a predetermined, substantially narrow particle size distribution range, is made under emulsion, dispersion or suspension polymerization conditions. The template particle can be comprised of any material that is able to be removed through heating, dissolution, or extraction following shell deposition. Preferably this template particle is a polymer latex particle, such as those comprising polystyrene or other styrenic polymers.

Figure 1:
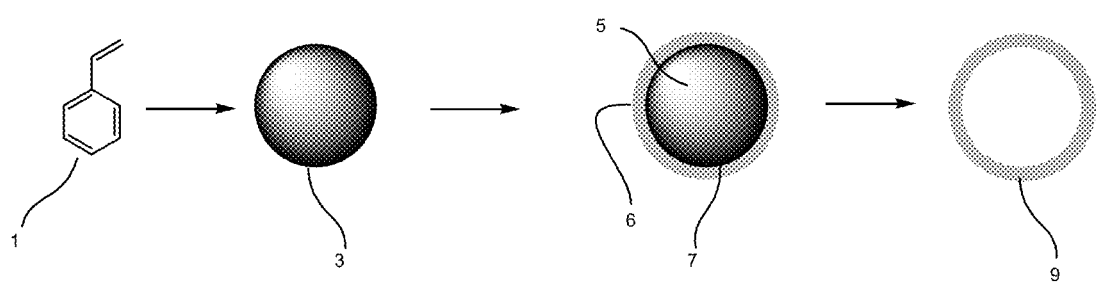
FIG. 1 is a schematic chemical reaction representation of one preferred method of the present invention.

As shown in FIG. 1, according to one preferred embodiment of the present invention, a template polystyrene particle 3 is prepared by polymerizing styrene 1 under certain conditions. Such reaction conditions include heat treatment, and addition of certain reactants. By selecting the appropriate reactant, concentration, temperature, and processing conditions, such as stir rate and stirrer design, template particles 3 are formed having a particle size that averages between about 200 nm and about 700 nm in diameter. Once the template particles 3 are formed, they are treated with a coupling agent followed by a silicon-containing compound or mixture of compounds under specific pH and temperature conditions to deposit a substantially uniform silica-containing coating 6 onto the particle template to form a coated particle 5 having a coating 6 and a polystyrene core 7. The coated particle 5 is then isolated and heated under specified conditions to eliminate the core 7, resulting in the desired end-product; a substantially uniform hollow silica particle 9 and a byproduct of styrene and styrene oxidation products (not shown in figure).

Figure 2:
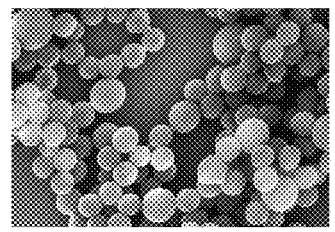
FIG. 2 is a photomicrograph showing the template particles formed according to one embodiment of the present invention.
Figure 3:
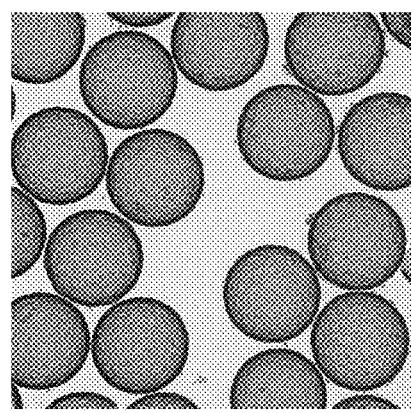
FIG. 3 is a photomicrograph of one embodiment of the present invention showing the hollow silica particles.

FIG. 2 is a photomicrograph showing polystyrene template particles prepared according to one embodiment of the present invention, which have an average diameter of about 500 nm and a narrow particle size distribution. Finally, FIG. 3 is a photomicrograph of the final product of the present invention; substantially uniform hollow silica particles having an average particle size of about 500 nm with a narrow particle size distribution.

In accordance with one preferred embodiment of the present invention, the preferred average template particle size, controlled by the emulsion, dispersion or suspension polymerization conditions, is preferably from about 200 nm to about 700 nm in diameter, and more preferably from about 250 to about 600 nm. The ideal particle size distribution is such that at least 25% of the particles are within the range of about 200 nm to about 700 nm, preferably at least 50%, as determined by image analysis. Thus the ideal distribution depends on the average particle size. The template particle can comprise any monomer or polymer material that allows for removal of the polymer core following shell deposition. Suitable template materials include styrenic polymers, acrylate polymers, and related copolymeric systems. Preferably, styrene, derivatives of styrene such as alphamethylstyrene, or mixtures of styrene and styrene derivatives are used as monomer in the emulsion, dispersion, or suspension polymerization reaction. More preferably, styrene is used as the sole monomer or styrene/alphamethylstyrene mixtures, and, even more preferably, styrene is used alone.

As outlined in FIG. 1, the preferred template latex is optionally synthesized in the absence of a surfactant, but it should be noted that the template synthesis can be carried out in the presence of any surfactant or mixture of surfactants that do not interfere with the emulsion, dispersion, or suspension polymerization reaction. Preferably, the surfactant or mixture of surfactants is anionic in nature. More preferably, the surfactant or mixture of surfactants is selected from alkyl sulfates, alkyl sulfonates, linear alkyl arylsulfonates, or a combination of any of these. Even more preferably, the surfactant is sodium dodecylsulfate, sodium dodecylbenzenesulfonate or a mixture thereof. Preferably, an initiator is added to the template particle synthetic reaction. Particularly preferred initiators include, but are not limited to, persulfate salts, organic hydroperoxides and, azo initiators.

The emulsion, dispersion, or suspension polymerization reaction is preferably carried out in a temperature range between preferably from about 25° C. to about 150° C., more preferably between from about 50° C. to about 100° C. and even more preferably at about 70° C. In one embodiment, surfactant is used in the preparation of the template particles. If surfactant is used, its identity and concentration are chosen such as to not significantly interfere with the subsequent shell deposition step, thus allowing the latex to be used as produced in the shell deposition step. Optionally, the surfactant can be removed by isolating and washing the template particles or by passage of the reaction mixture through a suitable ion-exchange resin before performing the shell deposition step, although this is not necessarily a preferred method. If this method is chosen, after the washing is complete, the latex template can be re-suspended in water. In another embodiment, the polystyrene latex is prepared in the absence of surfactant and is used as produced in the shell deposition step.

For the shell deposition step, the polystyrene latex mixture is typically diluted to a concentration appropriate for the shell deposition step. The concentration in percent solids is typically in the range of about 0.1 to about 50%, preferably from about 2 to about 30%. The polystyrene latex mixture is typically heated to elevated temperatures. For example, when tetraethoxysilane is used as the silicon-containing compound, the temperature is preferably in the range of from about 20° C. to about 150° C., more preferably between from about 45° C. to about 90° C. and even more preferably about 50° C.

Preferably, the pH is adjusted, with the ideal pH depending on the nature of the silicon-containing compound or mixture of compounds being added in the shell deposition step. For example, for tetraethoxysilane, the reaction mixture pH preferably is in the range of from about 8 to about 12, more preferably in the range of from about 9 to about 11, and even more preferably in the range of from about 10 to about 10.5. The pH adjustment can be achieved with any suitable acid (for the low pH preferred with certain silicon-containing compounds) or base known to those skilled in the art. For example, ammonium hydroxide is a preferred choice when a tetraalkoxysilane, such as tetraethoxysilane, is used.

After pH adjustment, but before adding the silica-containing compound to deposit the shell, it may be advantageous to add a compatibilizer, such as a silane coupling agent. Suitable compatibilizers for polystyrene template particles include phenyltrimethoxysilane, (3-aminopropyl) triethoxysilane, or a combination of the two. Any coupling agent capable of promoting the deposition of a silica-containing shell on the surface of the template particles can be used.

Following the addition of the coupling agent to the polystyrene latex mixture, the shell precursor silicon-containing compound(s) are added with stirring to deposit the silica-containing shell. The preferred silicon-containing material is a tetraalkoxysilane, such as tetraethoxysilane, tetrapropoxysilane or tetramethoxysilane, and is preferably tetraethoxysilane or tetramethoxysilane. Use of partially condensed alkoxysilanes, such as partially condensed ethoxysilanes and other alkoxy-containing oligomers or polymers are also considered to be within the scope of the current invention. The preferred rate of addition of the silicon-containing compound depends on the identity of the compound. For example, for tetraethoxysilane the addition is preferably done slowly, within 3 to 48 hours, preferably within about 24 hours. When the silicon-containing compound is tetramethoxysilane, the addition is preferably completed within 30 minutes to 16 hours. The silicon-containing compound can be diluted in a solvent prior to addition, such as in the case where tetraethoxysilane is diluted in ethanol, although this is not necessary. It may be desired to dilute the silicon-containing compound in an alcohol or alcohol mixture, however, with some tetraalkoxysilanes such as tetrapropoxysilane. The amount of silicon-containing compound that is added to the template particle dispersion, as a weight percent with respect to the weight of the template particles, depends on the chemical nature of the silicon-containing compound and the efficiency of the deposition. The ideal amount is the least amount required to isolate core/shell particles with the desired shell thickness and characterized by a sufficient purity for the desired application. The "desired shell thickness" is defined in terms of the final particle performance desired. For the application of the current invention, it is desired that the shells be thin enough to allow for the removal of the core, and also thick enough to withstand mechanical manipulation and subsequent formulation without losing structural integrity. The shells produced according to the present invention are typically between about 10 and about 30 nm thick, and more typically between about 15 and about 25 nm thick. After the addition of the silicon-containing compound is complete, the reaction can optionally be allowed to continue stirring before particle isolation.

The core/shell particles are isolated by either centrifugation or filtration. According to one embodiment of the present invention, centrifugation is preferred due to the superior ability to isolate more pure product devoid of solid, colloidal $SiO_2$. Indeed, according to one embodiment of the present invention, it is preferred that the centrifuge regimen is closely observed. No dual separation is needed, and the colloidal $SiO_2$ present in the optically clear mother liquor does not contaminate the isolated product with the centrifuge set to apply a force to the sample of from about 5,000 to about 20,000 g for a period of from about 5 minutes to about 1 hour, more preferably at a force of about 15,000 g for a period of from about 10 to about 15 minutes. Subjection of the particles in the reaction mixture to these centrifuge parameters results in a substantial amount of the colloidal $SiO_2$ being retained in suspension and poured off, leaving a more pure product in the sediment. Filtration is also an option, provided that the method allows for the isolation of particles that, in the end, provide the desired benefits. The core/shell particles can optionally be washed and reisolated, but this is not necessary.

After isolation of the coated particles, the core material is removed. Preferably, the removal is achieved by heating the core/shell particles in two stages. The first stage includes heating the particles to a temperature at which template depolymerization and volatilization is favored and holding the temperature substantially constant for a time sufficient to produce particles that are white in color and have the desired optical properties at the end of the completed heating regimen. After the first "hold" temperature, it is advantageous to heat the particles to a higher temperature for a time long enough to densify the shells. Obtaining the hollow particles that are white in color is a preferred embodiment of the present invention when the particles are to be incorporated into a cosmetic product. Particles having acceptable whiteness are characterized by TAPPI Brightness values (T-452 Brightness (1987) method) of preferably greater than or equal to about 0.5, more preferably greater than or equal to 0.55, and even more preferably greater than or equal to 0.6. It is also preferred that the hollow particles of the present invention be substantially impermeable to liquid penetration through the shell under conditions of use. Densification of the shell according to the core removal heating regimen of the present invention provides hollow particles having the desired impermeability.

There is no need to cool the material between stage one and stage two. The ideal stage one temperature depends on the identity of the monomer or monomer mixture as well as the characteristics of the resulting polymer used to prepare the template particles as well as the design and mass transport properties of the oven. For the case where polystyrene latex is used as the material for the template particles, stage one includes heating to a temperature preferably in a range of from about 325° C. to about 525° C., more preferably between from about 375° C. to about 475° C., and even more preferably to about 425° C. The sample is held at the stage one temperature for a time period preferably of from about 1 to about 8 hours, more preferably from about 2 to about 6 hours and even more preferably for about 4 hours. Regardless of whether the template particles are made from styrene or mixtures of derivatives thereof, the stage two temperature is preferably in the range preferably of from about 525° C. to about 900° C., preferably between from about 550° C. to about 700° C. and even more preferably about 600° C. The stage-two temperature is held for about 1 to 8 hours, preferably for about 2 to 6 hours. The desired length of time for which the temperature stages are held depends in part on the gas flow rate in the oven and other parameters that affect mass transfer and thus the suggested hold times are not meant to be limiting, but rather are offered as examples. The temperature ramp and decline rates are not critical to the performance of the final product, provided that the ramp rate(s) do not contribute to the introduction of color in the final product. Temperature ramp and decline rates are typically in the range from about 0.1° C./min to about 25° C./min, preferably in the range of from about 1° C./min to about 10° C./min. The heating steps can be carried out under an oxygen-containing atmosphere or an inert atmosphere. The flow rate of the atmosphere is not critical provided that it is sufficient to avoid deposition of template decomposition products onto the particles during the heat treatment, which would introduce unwanted color. An alternate core/shell particle heating system is a fluidized bed furnace, which can also be a preferred method of core removal. It is further understood that gas flow rate could be altered to improve core removal times, however practical flow rate limits would be readily understood by one skilled in the field to avoid loss of product due to the fact that the hollow particle product is lightweight. Alternatively, the core can be removed by dissolution or solvent extraction. If dissolution is used as the method for core removal, it may be advantageous to follow particle isolation with the stage two heating protocol to densify the shells.

It has now been determined that in one embodiment of the present invention that allows for the production of hollow silica particles with the desired properties for cosmetic applications includes the use of polystyrene latex, synthesized by emulsion, dispersion, or suspension polymerization, as the template particles. This preferred method allows for tight control over particle size and particle size distribution, which is important for achieving the desired optical effects of the resultant cosmetic product incorporating the particles of the present invention. This use of polystyrene latex further provides for the eventual removal of the template from the silica-coated core/shell product by heating. Further advantageous features include the use of a silane coupling agent to promote the deposition of silica on the core surface, as well as the controlled addition of the silicon-containing compound at a specific and controlled pH and temperature. Use of a compatibilizer as well as controlling the addition rate of the alkoxysilane, the reaction pH and the temperature allows for condensation and deposition of the silica on the surface of the particle to be sufficient relative to condensation/particle formation in the bulk solution. This is important because condensation of silica to form solid particles in the bulk solution does not yield a silica coated template and therefore, in the end, a hollow particle. Silica particles that are produced in the bulk solution are separated from the desired product according to one method of the present invention. Further, the heating protocol defined in this invention allows for the removal of the template material efficiently, without the introduction of unwanted color. Significantly, the method of the current invention allows for the isolation of hollow silica exhibiting low permeability to liquids such as, but not limited to, water and decamethylcyclopentasiloxane (sold commercially as SF1202, available from General Electric Company, NY) under conditions of use in cosmetic and other compositions. These aspects of hollow particle synthesis provide a material that, when formulated in certain media such as a cosmetic formulation, provide both enhanced coverage and perceptibly superior naturalness. The permeability of the particles of the present invention has been determined to be acceptable relative to specific permeability tests. To be acceptable for use in cosmetics, the finished hollow particles of the present invention must have extremely low permeability, or, in other words, be substantially impermeable to decamethylcyclopentasiloxane. The particles are said to be substantially impermeable to decamethylcyclopentasiloxane when about 90 to about 100% of a particle sample of from about 50 to 100 mg floats in a 10-15 mL sample of decamethylcyclopentasiloxane for a time period of at least about 30 days. Product satisfying this float test is known to display a useful shelf life of at least about 7 months when incorporated into a cosmetic product.

After isolation, the hollow particles may be functionalized by reaction with any monomeric, oligomeric or polymeric material, or mixture thereof, that is capable of reacting or interacting significantly with the surface of the hollow particles. For example, functional silanes, silazanes, or silicone oligomers or polymers can be allowed to react with surface silanols present on the particle surface. Such suitable materials include trialkoxy- or triaryloxysilanes, dialkoxy- or diaryloxysilanes, alkoxy- or aryloxysilanes, derivatives thereof (i.e., oligomeric or polymeric), or mixtures thereof, as well as reactive silicon-containing materials, such as hexamethyldisilazane. The functionality present on the reactive silane, oligomer or polymer can be chosen to modify the dispersibility of the particles, improve their stability in formulation, to improve their compatibility with other formulation ingredients, or provide functionality that adds other consumer appreciated benefits, such as optical or other sensory benefits (e.g. soft feel). In the case of alkoxysilanes or aryloxysilanes, additional functionality may be incorporated such as alkyl, aryl, olefin, ester, aine, acid, epoxide, alcohol and the like. One preferred functionalization reaction is that which occurs upon allowing the hollow silica particles to react with hexamethyldisilazane. This reaction can be carried out in a liquid reaction mixture or in the absence of solvent between the dry material and hexamethyldisilazane in the vapor state.

2. Cosmetic Composition

The hollow silica particles of the present invention may be used in cosmetic compositions. The hollow silica particles of the present invention are present in an amount of from about 0.01% to about 90%, more preferably from about 0.02% to about 50%, even more preferably from about 0.03% to about 25%, still more preferably from about 0.05% to about 15%, by weight of the composition.

The compositions of the present invention preferably comprise a colorant, such as a pigment or a dye. Pigments are defined as colorants that are insoluble in the medium in which they are being used. Thus, pigments do not substantially dissolve or are insoluble in product or usage. Often, pigments are slightly soluble in the product. This soluble portion of the pigment is referred to as free dye. Pigments include, but are not limited to, lakes and encapsulated colorants.

Dyes are colorants that are substantially soluble in the medium in which they are being used. The use of dyes is often intended to provide permanent, semi-permanent or durable color for the skin, or nails.

Some of the dyes which can be used herein include, but are not limited to, D&C Yellow No. 7, D&C Red No. 36, FD&C Red No. 4, D&C Orange No. 4, D&C Red No. 6, D&C Red No. 34, FD&C Yellow No. 6, D&C Red No. 33, FD&C Yellow No. 5, D&C Brown No. 1, D&C Red No. 17, FD&C Green No. 3, D&C Blue No. 4, D&C Yellow No. 8, D&C Orange No. 5, D&C Red No. 22, D&C Red No. 21, D&C Red No. 28, D&C Orange No. 11, D&C Yellow No. 10, D&C Violet No. 2, Ext. D&C Violet No. 2, D&C Green No. 6, D&C Green No. 5, D&C Red No. 30, D&C Green No. 8, D&C Red No. 7, FD&C Blue No. 1, D&C Red No. 27, D&C Orange No. 10, D&C Red No. 31, FD&C Red No.

40, D&C Yellow No. 11, CI 10020, CI 16185, CI 16255, CI 45430, CI 73015, CI 74160, carmine, and mixtures thereof.

Pigments may also be used alone or in combination with dyes. Some of these useful herein include, but are not limited to, aluminum powder, ultramarines, bismuth oxychloride, chromium oxide green, chromium hydroxide green, iron oxides, ferric ferrocyanide, manganese violet, titanium dioxide, zinc oxide, mica, bronze powder, copper powder, aluminum stearate, calcium stearate, magnesium stearate, zinc stearate, capsanthin/capsorubin, bentonite, barium sulfate, calcium carbonate, calcium sulfate, carbon black, magnesium carbonate, colored silica, lakes of dyes listed above, and mixtures thereof. Other suitable colorants and pigments may be found in the International Cosmetic Ingredient Dictionary and Handbook, Seventh Edition.

The compositions of the present invention can comprise any suitable optional ingredients, such as those described in U.S. patent application Ser. No. 10/840,833, filed May 7, 2004 and published as U.S. Application Publication No. 2003/0003064A1 on Jan. 2, 2003. Optional ingredients can include, but are not limited to, volatile, or non-volatile carriers, polar or non polar carriers such as aqueous carriers, silicone carriers, hydrocarbon carriers, wax carriers, and other described in U.S. Pat. No. 6,696,049, desquamation actives (such as those disclosed in U.S. Pat. No. 5,681,852), anti-acne actives, antiperspirant actives, anti-wrinkle/anti-atrophy actives, anti-oxidants/radical scavengers, chelators, flavonoids (such as those disclosed in U.S. Pat. Nos. 5,686,082 and 5,686,367), anti-inflammatory agents, anti-cellulite agents, topical anesthetics, tanning actives, skin lightening agents (such as those described in PCT Publication No. 95/34280, PCT Application No. 95/07432, and PCT Publication No. 95/23780), skin soothing actives, skin healing actives, antimicrobial actives, antifungal actives, sunscreen actives (such as those disclosed by Sagarin, et al., at Chapter VIII, pages 189 et seq., of *Cosmetics Science and Technology* (1972)), particulate materials (such as those disclosed in U.S. Pat. No. 5,997,887), conditioning agents (such as those described in U.S. Pat. No. 4,976,953), thickening agents (such as those described in U.S. Pat. Nos. 5,087,445, 4,509,949, 2,798,053, and in *CTFA International Cosmetic Ingredient Dictionary*, Fourth Edition, 1991, pp. 12 and 80; U.S. Pat. Nos. 5,100,660, 4,849,484, 4,835,206, 4,628,078, 4,599,379, EP 228,868, U.S. Pat. Nos. 5,654,362 and 5,880,210; Warth, *Chemistry and Technology of Waxes*, Part 2, Reinhold Publishing, 1956)), additional powdered ingredients (such as those described in C.T.F.A. *Cosmetic Ingredient Handbook*, First Edition, Washington D.C. (1988), and in U.S. Pat. No. 5,505,937), materials for enhancing wear or transfer resistance (such as those disclosed by E. S. Barabas in the *Encyclopedia of Polymer Science and Engineering*, 2 Ed., Vol. 17, pp. 198-257; PCT Publication Nos. WO96/33689 and WO97/17058, and U.S. Pat. No. 5,505,937, PCT publication No. WO98/18431, and US Patent No. 5,800), emulsifiers (such as those described by Wilkinson and Moore, *Harry's Cosmeticology*, 7th Ed. 1982, p. 738; Schick and Fowkes, Surfactant Science Series, Vol. 2, *Solvent Properties of Surfactant Solutions*, p 607; C.T.F.A. Cosmetic Ingredient Handbook, 3rd Ed., Cosmetic and Fragrance Assn., Inc., Washington D.C. (1982) pp. 587-592; Remington's Pharmaceutical Sciences, 15th Ed. 1975, pp. 335-337; McCutcheon's Volume 1, *Emulsifiers & Detergents*, 1994, North American Edition, pp. 236-239, U.S. Pat. Nos. 4,268,499, and 5,143,722), and co-solubilizers (such as those described by U.S. Pat. Nos. 4,268,499 and 5,143,722).

The advantages of the synthetic method described herein include predictable control of particle size, control of shell thickness, the ability to functionalize the surface, and the ability to create a continuous shell having a substantially uniform thickness. The performance benefits in personal care products afforded by the particles of the present invention include, for example, high coverage and a natural look when formulated as a cosmetic product. The ability to functionalize the surface of the particles offers advantages in particle dispersibility, stability in and out of formulation, compatibilization, and the ability to add additional consumer relevant benefits, such as optical effects.

The hollow silica particles or "shells" of the present invention may also be useful as fillers for various polymers, in order to modify the density, thermal behavior, optical properties, viscosity, processability, or other physical properties. The shells may also be useful as templates or supports for the growth of shells of other materials, such as metallic shells. The metallic shells may comprise Cu, Ag, Au, and the like, the properties of which are dependent upon the metal shell thickness.

Deposited/grafted/reacted shells may also be polymeric in nature. Therefore, the present invention further contemplates the presence of a plurality of coatings over the particle template. The template may be removed after a single coating has been deposited onto the first coating. In addition, a plurality of coatings may be deposited over the particle template core before removal of the core, provided that they do not prevent the removal of the core. In the case where a metallic layer may be employed, it is to be understood that the present invention contemplates the deposition of the metallic and non-metallic layers in any useful order depending upon the desired resulting effect.

The cosmetic compositions of the invention may be of a wide variety of product forms. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes. Suitable personal care product forms are disclosed in U.S. Pat. Nos. 6,071,503, 6,139,823, 6,019,962, 6,106,820, 6,017,552, 6,013,269, and 6,001,373.

EXAMPLES

Example 1

Foundation

| Ingredients | Wt. % |
|---|---|
| Hollow Silica Particles | 10% |
| Cyclopentasiloxane & Dimethicone copolyol | 10% |
| Cyclopentasiloxane | q.s. |
| Yellow Iron Oxide 55% Slurry - Kobo | 0.51% |
| Black Iron Oxide 65% Slurry - Kobo | 0.1% |
| Red Iron Oxide 70% Slurry - Kobo | 0.46% |
| Water | 5% |
| Preservative | 0.75% |
| Glycerin | 5% |
| Cyclopentasiloxane & Dimethicone crosspolymer | 43% |

First prepare "phase A" by combining hollow silica, pigments, cyclopentasiloxane, and dimethicone copolyol. Mill until well dispersed. Next prepare "phase B" by mixing water, glycerin, and preservatives until uniform, heating if necessary. Add phase B to phase A and mill until uniform. Add dimethicone crosspolymer and mix until uniform. Make one pass of the sample through 3 roll-mill.

Example 2

Foundation

| Ingredients | Wt. % |
| --- | --- |
| Hollow Silica Particles | 10% |
| Cyclopentasiloxane & Dimethicone copolyol | 10% |
| Dimethicone Fluid | 10% |
| Cyclopentasiloxane | q.s. |
| Yellow Iron Oxide 55% Slurry - Kobo | 0.51% |
| Black Iron Oxide 65% Slurry - Kobo | 0.1% |
| Red Iron Oxide 70% Slurry - Kobo | 0.46% |
| Preservative | 0.75% |
| Water | 5% |
| Glycerin | 5% |
| Cyclopentasiloxane & Dimethicone crosspolymer | 43% |

First prepare "phase A" by combining hollow silica, pigments, cyclopentasiloxane, dimethicone fluid, and dimethicone copolyol. Mill until well dispersed. Next prepare "phase B" by mixing water, glycerin, and preservatives until uniform, heating if necessary. Add phase B to phase A and mill until uniform. Add dimethicone crosspolymer and mix until uniform. Make one pass of the sample through 3 roll-mill.

Example 3

Foundation

| Ingredients | Wt. % |
| --- | --- |
| Water | 52.5% |
| Hollow Silica Particles | 10% |
| Untreated Yellow Iron Oxide | 0.3% |
| Untreated Black Iron Oxide | 0.06% |
| Untreated Red Iron Oxide | 0.3% |
| Cyclomethicone | q.s. |
| Cyclopentasiloxane & Dimethicone copolyol | 15% |
| Preservative | 0.47% |

First prepare "phase A" by mixing hollow silica particle and untreated pigments with water and mill until particles are well dispersed. Next prepare "phase B" by mixing cyclomethicone, cylopentasiloxane & dimethicone copolyol, and preservative with mixer until homogeneous. Slowly add Phase A to Phase B, and mix until uniform.

Example 4

Water Continuous Foundation

| Ingredients | Wt. % |
| --- | --- |
| Water | 68.2% |
| Glycerin | 5% |
| 2-amino-2-methyl-1-propanol | 0.5% |
| Preservatives | 0.75% |
| Ethyl Paraben | 0.2% |
| Hollow silica particles | 10% |
| Untreated Red Iron Oxide | 0.3% |
| Untreated Black Iron Oxide | 0.06% |
| Untreated Yellow Iron Oxide | 0.3% |
| Polyacrylamide | 0.5% |
| dimethincone/vinyl dimethicone crosspolymer and cyclopentasiloxane | 12% |

Mix water, glycerin, hollow silica particles and untreated pigments, and mill until uniform. Add polyacrylamide to water phase mixture. Add remaining ingredients and mix.

Examples 5-8

Water in Silicone Foundation

| Ingredients | 5 Wt. % | 6 Wt. % | 7 Wt. % | 8 Wt. % |
| --- | --- | --- | --- | --- |
| Oil Phase | | | | |
| Emulsifiers | 2.50 | 2.50 | 2.50 | 2.50 |
| Volatile Silicones | 28.00 | 28.00 | 28.00 | 28.00 |
| Non-volatiles | 5.00 | 5.00 | 5.00 | 5.00 |
| Pigment/colorants/Fillers | 7.00 | 7.00 | 7.00 | 7.00 |
| Hollow silica | 10 | 10 | 8 | 8 |
| Rheological Additives/Fragrance/Preservatives | 1.00 | 1.00 | 1.00 | 1.00 |
| Aqueous Phase | | | | |
| Polyquaternium-6** | 1.50 | 1.00 | 2.00 | 1.25 |
| Preservatives | 0.5 | 0.5 | 0.5 | 0.5 |
| Propylene glycol | 5.00 | 5.00 | 5.00 | 5.00 |
| Water | q.s. | q.s. | q.s. | q.s. |

**Merquat 100 as received - Nalco Chemical Company

Prepare foundations by dispersing or mixing colorants/pigments/fillers and hollow silica in silicone phase using a high speed disperser, mill, or other methods known in the art to ensure uniform color and efficient use of colorant. Add remainder of additives with heat if necessary to ensure solid waxes are melted. Combine all aqueous phase ingredients with mixing adding the polymer after other ingredients have been dissolved. Cool phases to room temperature if necessary. Slowly add aqueous phase to silicone phase, mixing with stirrer, homogenizer, or other methods know in the art to form emulsion. Final emulsion properties can be modified or adjusted as would be evident to one skilled in the art.

Example 9

Moisturizer/Tinted Moisturizer

| Ingredients | Wt % | Wt % | Wt % |
| --- | --- | --- | --- |
| Hollow Silica Particles | 0.5 | 0.5 | 2 |
| Cyclopentasiloxane & Dimethicone crosspolymer | 45.00 | 45.00 | 45.00 |
| Cyclopentasiloxane & Dimethicone copolyol | 5.00 | 5.00 | 5.00 |
| Cyclomethicone | q.s. | q.s. | q.s. |
| Yellow Iron Oxide 55% Slurry - Kobo | | 0.1 | 0.4 |
| Black Iron Oxide 65% Slurry - Kobo | | 0.03 | 0.12 |
| Red Iron Oxide 70% Slurry - Kobo | | 0.04 | 0.16 |
| Preservatives | 0.7 | 0.7 | 0.7 |

-continued

| Ingredients | Wt % | Wt % | Wt % |
|---|---|---|---|
| Water | 15.00 | 15.00 | 15.00 |
| Glycerin | 10.00 | 10.00 | 10.00 |

First prepare "phase A" by mixing hollow silica particles, pigments, silicone copolyol crosspolymer, and optionally silicone phase preservatives, with the cyclopentasiloxane. Mill until the hollow silica particles are well dispersed. Next, prepare "phase B" by mixing water, glycerin, and preservatives until uniform, heating if necessary. Add phase B to phase A, and mill until uniform. Add Dimethicone crosspolymer, and mix until uniform. Make one pass of the sample through 3 roll-mill.

Example 10

Lipstick

| Ingredients | Wt. % |
|---|---|
| Isopropyl Isostearate | 15 |
| Octyl Hydroxystearate | 8.5 |
| Acetylated Lanolin | 6.33 |
| Ozokerite was | 5 |
| Candelilla wax | 3 |
| Paraffin Wax | 2.5 |
| Carnauba Wax | 2 |
| Cetyl Alcohol | 2 |
| Cetyl Lactate | 2 |
| Ascorbyl Palmitate | 0.5 |
| Propylparaben | 0.1 |
| Hollow silica particles | 4 |
| Pigments/colorants/fillers | 10 |
| Castor Oil | q.s. |

Mix ingredients under low shear with heat (~70-80° C.) until uniform. Remove air under reduced pressure. Pour molten mixture into mold, then cool. Remove from mold and place in appropriate package.

Example 11

Liquid Lip Color

| Ingredients | Wt. % |
|---|---|
| Organo silioxane resin (MQ resin 0.7:1 M:Q ratio - GE) | 20.84 |
| Dimethicone gum (100,000-1,000,000 cSt - GE) | 14.03 |
| Hectorite clay | 3.09 |
| Propylene Carbonate | 0.93 |
| Isododecane | q.s. |
| Hollow silica | 4 |
| Pigments/colorants/fillers | 10 |

Dissolve MQ resin and Dimethicone gum into the appropriate amount of isododecane solvent. Mill isododecane, hectorite clay, and propylene carbonate into a paste. Combine the paste, resin and gum mixture, then mill. Add hollow silica, pigments/colorant/fillers to the above mixture and mill until uniform.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

The invention claimed is:

1. A method of making a cosmetic composition comprising a hollow, low permeable silica particle, comprising the step of adding: a colorant; a cosmetically-suitable decamethylcyclopentylsiloxane carrier, and a plurality of hollow silica particles comprising a silicon-containing compound selected from the group consisting of tetraalkoxysilanes, trialkyloxysilanes and derivatives thereof, dialkoxysilanes and derivatives thereof, alkoxysilanes and derivatives thereof, silicone oligomers, oligomeric silsesquioxanes and silicone polymers, said hollow silica particles having an average particle size of 500 nm; wherein said hollow silica particles have a shell thickness from about 15 to about 25 nm and are spherical and 90% to 100% of a particle sample of 50 to 100 mg floats in decamethylcyclopentyl siloxane for a time period of at least 30 days.

2. The method of claim 1, further comprising a plurality of coatings, each coating having a constant thickness.

3. The method of claim 1, wherein said hollow silica particle comprises an outer surface functionalized with a material comprising organosilyl groups.

4. The method of claim 1, wherein said hollow silica particle comprises an outer surface functionalized by reacting said surface with hexamethyldisilazane.

5. The method of claim 1, wherein said hollow silica particle further comprises a chemical functionality selected from the group consisting of olefins, esters, amines, acids, epoxides, alcohols, and mixtures thereof.

6. The method of claim 1, wherein said at least one coating comprises a metallic formulation.

7. The method of claim 6, wherein said metallic formulation comprises a material selected from the group consisting of copper-containing compounds, silver-containing compounds, gold-containing compounds, and mixtures thereof.

8. The method of claim 1, wherein said colorant is selected from the group consisting of pigments and dyes.

9. The method of claim 1, wherein said hollow silica-containing particle is present in an amount of from about 0.01% to about 90% by weight of the composition.

10. The method of claim 1, wherein said hollow silica-containing particle is present in an amount of from about 0.02% to about 50% by weight of the composition.

11. A cosmetic composition comprising a hollow, low permeable silica particle made according to the method of claim 1.

* * * * *